United States Patent [19]

Haviv et al.

[11] Patent Number: 4,489,084
[45] Date of Patent: Dec. 18, 1984

[54] [1-(2-OXAZOLYL) OR -(2-THIAZOLYL) HYDRAZINO]ALKYL NITRILES

[75] Inventors: Fortuna Haviv, Deerfield; Francis A. J. Kerdesky, Vernon Hills, both of Ill.

[73] Assignee: Abbott Laboratories, North Chicago, Ill.

[21] Appl. No.: 509,750

[22] Filed: Jun. 30, 1983

[51] Int. Cl.³ .................. C07D 263/20; C07D 277/38; A61K 31/42; A61K 31/425
[52] U.S. Cl. .................... 424/270; 424/272; 548/193; 548/198; 548/233
[58] Field of Search ............. 548/198, 233, 193; 424/270, 272

[56]  References Cited
U.S. PATENT DOCUMENTS 3,328,416  6/1967  Wilhem .............................. 548/198

Primary Examiner—Robert Gerstl
Attorney, Agent, or Firm—Martin L. Katz; Dennis K. Shelton

[57] ABSTRACT

Described are oxazolyl (or thiazolyl) hydrazinoalkyl nitrile compounds of the formula

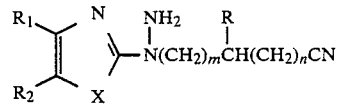

wherein R is hydrogen or loweralkyl, $R_1$ and $R_2$ independently of one another denote hydrogen, loweralkyl, or phenyl or naphthyl substituted with halo, loweralkyl or loweralkoxy, X is oxygen or sulfur, n and m are each an integer from 0 to 3 inclusive, or pharmaceutically acceptable salts thereof. The compounds are useful as anti-inflammatory agents.

23 Claims, No Drawings

[1-(2-OXAZOLYL) OR -(2-THIAZOLYL) HYDRAZINO]ALKYL NITRILES

BACKGROUND AND SUMMARY OF THE INVENTION

The present invention relates to oxazolyl (or thiazolyl)-hydrazinoalkyl nitrile compounds and compositions. The compound and compositions exhibit anti-inflammatory activity and are useful for the treatment of rheumatoid arthritis, type III hypersensitivity diseases, diseases in which polymorphonuclear leukocyte accumulation contributes to the pathology, and other inflammatory conditions.

The present invention is directed to compounds of the formula

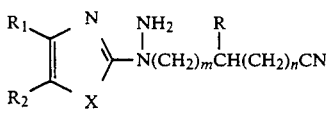

wherein R is hydrogen or loweralkyl; $R_1$ and $R_2$ independently of one another denote hydrogen, loweralkyl, or phenyl or naphthyl substituted with halo, loweralkyl or loweralkoxy, X is oxygen or sulfur, n and m are each an integer from 0 to 3 inclusive, or pharmaceutically acceptable salts thereof. In another one of its aspects, the present invention is directed to pharmaceutical compositions comprising a compound of formula I together with a pharmaceutically acceptable carrier. In yet another one of its aspects the present invention is directed to a method of treating or relieving the symptoms associated with inflammation comprising administering to a patient in need of such treatment a therapeutically effective amount of a compound of formula I.

DETAILED DESCRIPTION OF THE INVENTION

The term "loweralkyl" as used herein refer to straight or branched chain alkyl radicals containing from 1 to 6 carbon atoms including but not limited to methyl, ethyl, n-propyl, iso-propyl, n-butyl, sec-butyl, tert-butyl, n-pentyl, 1-methylbutyl, 2,2-dimethylbutyl, 2-methylpentyl, 2,2-dimethylpropyl, n-hexyl and the like.

The term "loweralkoxy" as used herein refers to alkoxy radicals of the formula $-OR_3$ wherein $R_3$ is loweralkyl.

The term "halo" as used herein refers to chloro, bromo, fluoro and iodo.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, and like salts. Also included are metallic salts such as the sodium or potassium salt of the acid.

The present compounds may be administered to warm-blooded animals orally or parenterally. They can generally be administered with a pharmaceutical carrier. The term "pharmaceutically acceptable carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition comprising a compound of the invention together with a pharmaceutically acceptable carrier can be administered to warm-blooded animals in parenteral or oral dosage form. For oral administration, amounts of from about 0.1 to 200 mg. of active compound per kg. of body weight per day per patient are useful, with the total dose of up to 0.5 to 5.0 gm. per day being a suitable range for large animals, including humans. The total dose may be divided for multiple administration, for example, two to four times per day.

For all dosage forms, the above exemplified compounds can be placed in capsules, formulated into pills, wafers or tablets in conventional fashion together with pharmaceutical carriers well known in the art. Tablets may be prepared for immediate release of the active compound, for delayed release of the active compound or with an enteric coating for release within the intestinal tract.

Compounds of Formula I can be prepared by the reaction of the appropriate hydrazino compound with acrylonitrile in absence or in the presence of a solvent such as dioxane, tetrahydrofuran, diglyme, methylene chloride and in the presence of a base such as choline, sodium hydroxide, sodium ethoxide, etc., at temperatures varying from room temperature to 150° C. Another route for preparing compounds of Formula I is by reacting the appropriate 2-chlorooxazole derivative with 3-hydrazinopropanenitrile in dioxane and in the presence of one equivalent of base such as triethylamine. The 3-hydrazinopropanenitrile can be prepared in situ by the reaction of hydrazine with acrylonitrile.

In order to illustrate the manner in which the above compounds may be prepared and the properties of the compounds, reference is made to the following examples, which, however, are not meant to limit or restrict the scope of the invention in any respect.

EXAMPLE 1

3-[1-(2-Oxazolyl)hydrazino]propanenitrile hydrochloride

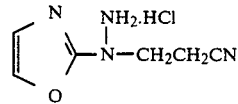

A solution of 2-chlorooxazole (1.3 g) in dioxane (250 ml) was added dropwise at room temperature to a solution of hydrazine hydrate (5 g). The reaction was refluxed for 12 hours. The hydrazine was removed in vacuo and the residue dissolved in THF (100 ml). Two drops of 2N sodium hydroxide solution were added and the solution was refluxed for 12 hours after addition of acrylonitrile (1.06 g). The THF was removed in vacuo and the residue was treated with ethereal hydrogen chloride to form the hydrochloride salt. This was crystallized from ethanol to give 3-[1-(2-oxazolyl)hydrazino]propanenitrile hydrochloride, m.p. 160°–162° C.

EXAMPLE 2

3-[1-(2-Thiazolyl)hydrazino]propanenitrile hydrochloride

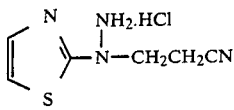

A solution of 2-aminothiazole (10 g) in 2N hydrochloric acid (80 ml) was treated with aqueous solution (10 ml) of sodium nitrite (7 g) at −10° C. and stirred for 40 minutes. The diazonium salt solution was subsequently reduced at the same temperature with a solution of stannous chloride (45 g) in 12N HCl (20 ml) over a period of 45 minutes. The precipitate was filtered, dried and washed with ether. This precipitate was suspended in benzene (100 ml) and water (10 ml). Ammonia gas was passed through the suspension for 1 hour. The benzene solution was decanted, dried over MgSO₄, filtered and concentrated in vacuo. The obtained residue was triturated with petroleum ether to give 2-hydrazinothiazole (7 g), m.p. 97°–98° C.

To a solution of 2-hydrazinothiazole (1.15 g) in tetrahydrofuran (50 ml) was added dropwise acrylonitrile (1 g) and ten drops of 2N sodium hydroxide solution. The reaction solution was refluxed for 12 hours. The solvent was removed in vacuo. The residue was dissolved in ethanol saturated with hydrochloric gas. The insoluble material was filtered and to the filtrate was added ether to give 3-[1-(2-thiazolyl)-hydrazino)]propanenitrile hydrochloride, m.p. 158°–159° C.

EXAMPLE 3

3-[1-(4-Phenyl-2-oxazolyl)-hydrazino]propanenitrile hydrochloride

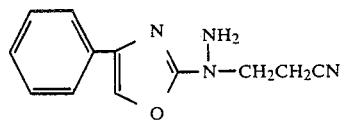

A solution of α-bromoacetophenone (19.9 g) and acetylsemicarbazide (10.7 g) in ethanol (300 ml), containing 1N hydrochloric acid (1 ml), was refluxed for thirty hours. The solvent was removed in vacuo and the residue was crystallized from ether-ethanol to give 2-hydrazino-4-phenyloxazole hydrochloride. This salt was suspended in an aqueous solution of 10% ammonium hydroxide to give 2-hydrazino-4-phenyloxazole, m.p. 158°–160° C.

To a solution of 2-hydrazino-4-phenyloxazole (1.75 g) in tetrahydrofuran (100 ml) was added acrylonitrile (1.1 g) and ten drops of 2N sodium hydroxide. The solution was refluxed for 12 hours. The solvent was removed in vacuo. The residue was treated with ethanol saturated with hydrochloric gas. The insoluble compound was removed by filtration and to the filtrate was added ether to give 3-[1-(4-phenyl-2-oxazolyl)hydrazino]propanenitrile hydrochloride, m.p. 170°–172° C.

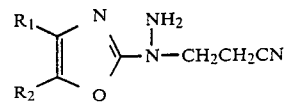

When the procedure described in Example 3 is applied to the bromoketones described below, the following oxazolylhydrazinopropanenitrile derivatives are obtained.

| Bromoketones | Products |
|---|---|
| 1-bromo-2-propanone | 3-[1-(4-methyl-2-oxazolyl)hydrazino]propanenitrile hydrochloride, m.p. 155–157° C. |
| 3-bromo-2-butanone | 3-[1-(4,5-dimethyl-2-oxazolyl)hydrazino]propanenitrile hydrochloride, m.p. 162–164° C. |
| 1-bromo-2-butanone | 3-[1-(4-ethyl-2-oxazolyl)hydrazino]propanenitrile hydrochloride |
| 3-bromo-2-pentanone | 3-[1-(4-methyl-5-ethyl-2-oxazolyl)hydrazino]propanenitrile hydrochloride |
| α-bromo-para-methoxy acetophenone | 3-[1-(4-para-methoxyphenyl-2-oxazolyl)hydrazino]propanenitrile hydrochloride |
| α-bromo-meta-methoxy acetophenone | 3-[1-(4-meta-methoxyphenyl-2-oxazolyl)hydrazino]propanenitrile hydrochloride |
| 1-(para-chlorophenyl)-2-bromo-1-propanone | 3-[1-(4-para-chlorophenyl-5-methyl-2-oxazolyl)hydrazino]propanenitrile hydrochloride |
| α-bromo-para-methylacetophenone | 3-[1-(4-para-methylphenyl-2-oxazolyl)hydrazino]propanenitrile hydrochloride |
| α-bromo-ortho-methylacetophenone | 3-[1-(4-ortho-methylphenyl-2-oxazolyl)hydrazino]propanenitrile hydrochloride |
| α-bromo-2'-acetonaphtone | 3-[1-[4-(2'-naphthyl)-2-oxazolyl]hydrazino]propanenitrile hydrochloride |
| α-bromo-6'-methoxy-2'-acetonaphtone | 3-[1-[4-(6'-methoxy-2'-naphthyl)-2-oxazolyl]hydrazino]propanenitrile hydrochloride. |

EXAMPLE 5

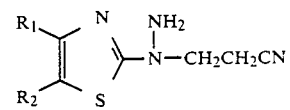

When the procedure described in Example 2 is applied to the 2-aminothiazoles described below, the following products are obtained:

| 2-Aminothiazoles | Products |
|---|---|
| 4-phenyl-2-aminothiazole | 3-[1-(4-phenyl-2-thiazolyl)-hydrazino)]propanenitrile hydrochloride |
| 4,5-dimethyl-2 aminothiazole | 3-[1-(4,5-dimethyl-2-thiazolyl)hydrazino]propanenitrile hydrochloride |
| 4-phenyl-5-methyl-2-aminothiazole | 3-[1-(4-phenyl-5-methyl-2-thiazolyl)hydrazino]propanenitrile hydrochloride |
| 4-(para-methoxyphenyl)-2-aminothiazole | 3-[1-(4-para-methoxyphenyl-2-thiazolyl)hydrazino]propanenitrile hydrochloride |
| 4-(para-methylphenyl)-2-aminothiazole | 3-[1-(4-para-methylphenyl-2-thiazolyl)hydrazino]propanenitrile hydrochloride |
| 4-(meta-chloro- | 3-[1-(4-meta-chlorophenyl)-2- |

-continued

| 2-Aminothiazoles | Products |
|---|---|
| phenyl)-2-amino-thiazole | thiazolyl)hydrazino]propane-nitrile hydrochloride |
| 4-(6'-methoxy-2'-naphtyl)-2-amino-thiazole | 3-[1-(4-(6'-methoxy-2'-naphtyl)-2-thiazolyl)hydrazino]propane-nitrile hydrochloride |

EXAMPLE 6

3-[1-(4,5-diphenyl-2-oxazolylhydrazino)]propanenitrile hydrochloride

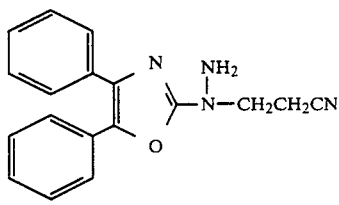

A mixture of 4,5-diphenyl-2-oxazolone (23.7 g), phosphorus oxychloride (90.6 g), and triethylamine (10.1 g) was refluxed for 10 hours. The excess of reagents were removed by distillation. The oily residue was dissolved in dioxane (50 ml) and added dropwise to a solution of hydrazine hydrate (25 g) in dioxane (150 ml). The solution was refluxed for 10 hours. The solvent and the excess of reagent were removed in vacuo to give after crystallization from ethanol-ether 4,5-diphenyl-2-hydrazinooxazole, m.p. 88°–89° C.

To a solution of 4,5-diphenyl-2-hydrazino-oxazole (2.5 g) in tetrahydrofuran (100 ml) was added acrylonitrile (1.1 g) and ten drops of 2N sodium hydroxide solution. The reaction mixture was refluxed for 12 hours. The solvent was removed in vacuo and the residue was dissolved in ethanol saturated with hydrochloric gas. Insoluble compound was removed by filtration. The filtrate was concentrated in vacuo and the residue was crystallized from ethanol-ether to give 3-[1-(4,5-diphenyl-2-oxazolylhydrazino)]propanenitrile hydrochloride, m.p. 168°–170° C.

EXAMPLE 7

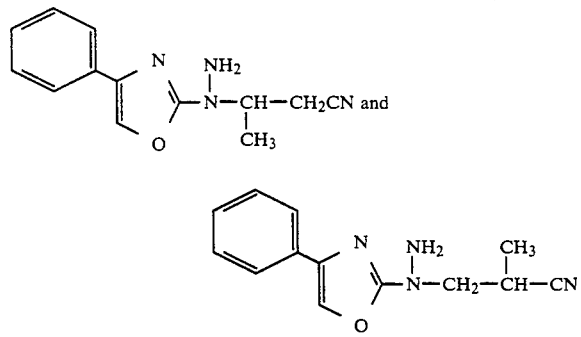

When in the procedure described in Example 3 acrylonitrile was replaced separately by methacrylonitrile and crotononitrile, 3-[1-(4-phenyl-2-oxazolyl)hydrazino]-2-methylpropanenitrile hydrochloride and 3-[1-(4-phenyl-2-oxazolyl)hydrazino]-3-methylpropanenitrile hydrochloride respectively are obtained.

The compounds of the present invention have anti-inflammatory activity and inhibitory effect against Type III hypersensitivity reaction. These compounds are useful for the therapy of rheumatoid arthritis, other inflammatory conditions, Type III hypersensitivity diseases and in diseases in which polymorphonuclear leukocytes accumulation contributes to the pathology.

The anti-inflammatory activity of these compounds was established by using a modification of the carrageenin pleurisy assay described by Vinegar et al. Proc. Soc. Exp. Biol. Med. 143:711 (1973). Table 1 shows the reduction in accumulation of exudate volume and leukocytes.

TABLE I

| Compound | Dose | % Inhibition | |
|---|---|---|---|
| | | Volume exudates | Cells |
| Phenylbutazone | 100 | 59 | 13 |
| 3-[1-(2-oxazolyl)-hydrazino]propane-nitrile | 100 | 32 | 21 |

The ability of these compounds to inhibit Type III hypersensitivity reactions was demonstrated using the reverse passive Arthus assay as described by Carter and Krause, Fed. Proc. 35, 774 (1976). Each compound was administered orally to a group of four animals.

The Arthus reaction represents one of the oldest and best studied models of immunological injury. It is produced by the injection of antigen locally into a hyperimmunized animal or by the injection of a small amount of antibody into the skin of an animal that has just previously been given a large amount of soluble antigen intravenously. In both cases the antigen and antibody become deposited in the walls of small venules. Plasma complement is rapidly bound and activated. Within a few hours neutrophils (PMNs) accumulate resulting in disruption of the basement membrane of vessel walls and marked edema and hemorrage in the surrounding tissue.

Although the etiology of rheumatoid arthritis remains obscure, it is almost certain that immunological mechanisms play an important role in the pathogenesis of this disease. Therefore, inflammation induced by immunological reactions, which are believed to be important in the inflammatory processes of rheumatoid arthritis, make particularly desirable tools for the screening of potential anti-inflammatory agents. The usefulness of such a model depends upon how closely it represents the underlying pathological mechanisms of rheumatoid arthritis.

Based upon currently available evidence, a plausible sequence of events leading to the joint leisions in rheumatoid arthritis can be constructed. An initiating antigen, perhaps a transient synovial infection, results in an immune response and retention of the antigen within the joint structure. The interaction of antigen with developing antibodies results in the deposition of immune complexes. These complexes may fix and activate complement, causing the generation of a number of phlogistic and chemotactic substances. Phagocytosis of the complexes by attracted polymorphonuclear leukocytes (PMNs) leads to the release of lysosomal constituents. The enzymes released from lysosomes can erode articular cartilage and produce inflammation in the joint. The striking resemblance of these events to the Arthus phenomenon point to the utility of the Arthus reaction as a screen for anti-inflammatory compounds.

The reserve passive Arthus reaction test in rats is conducted as follows: Male Sprague-Dawley rats weighing approximately 130–160 g. are used, 4 rats per group. All animals are injected intravenously with 0.5 ml. 0.075% Bovine Serum Albumin (B.S.A.) +2% Evans Blue solution. Each rat then receives an oral dose of drug; one drug is administered per group.

Thirty minutes subsequent to drug dosing, each animal is injected intradermally with 0.05 ml. 1.44% AntiB.S.A. into the dorsal skin. Four hours later the animals are sacrificed, the dorsal skin reflexed, and the lesion excised. Two perpendicular diameters of each lesion are measured. The average diameters of the lesions from the treated groups are compared with the average diameters from the control group to determine any drug effect.

The ability of these compounds to inhibit Type III hypersensitivity reactions was demonstrated using the reverse passive Arthus assay as described by Carter and Krause [Fed. Proc. 35, 774 (1976)]. Each compound was administered orally to a group of four animals. Table II shows the percentage of reduction in lesion area produced by representative compounds.

TABLE II

| Compound | Dose mg/kg | % Inhibition of lesion of dermal Arthus reaction |
|---|---|---|
| 3-[1-(4-phenyl-2-oxazolyl)hydrazino]-propane nitrile | 100 | 59 |
| 3-[1-(2-oxazolyl)-hydrazino]propane nitrile | 100 | 42 |
| 3-[1-(4,5-diphenyl-2-oxazolyl)hydrazino]-propane nitrile | 100 | 40 |
| 3-[1-(4,5-dimethyl-2-oxazolyl)hydrazino]-propane nitrile | 100 | 38 |
| Phenylbutazone | 100 | Inactive |

What is claimed is:

1. A compound of the formula

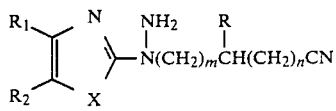

wherein R is hydrogen or loweralkyl, $R_1$ and $R_2$ independently of one another denote hydrogen, loweralkyl, or phenyl or naphthyl substituted with halo, loweralkyl or loweralkoxy, X is oxygen or sulfur, n and m are each an integer from 0 to 3 inclusive, or pharmaceutically acceptable salts thereof.

2. A compound of the formula

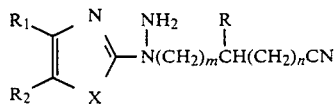

wherein R is hydrogen or loweralkyl, $R_1$ is hydrogen, loweralkyl, phenyl, chlorophenyl, methylphenyl, methoxyphenyl, naphthyl or methoxynaphthyl, $R_2$ is hydrogen or loweralkyl, X is oxygen or sulfur, n is 1 and m is 0, or pharmaceutically acceptable salts thereof.

3. A compound of the formula

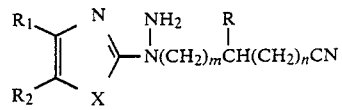

wherein R is hydrogen, $R_1$ and $R_2$ independent of one another denote hydrogen, loweralkyl or phenyl, X is oxygen or sulfur, n is 1 and m is 0, or pharmaceutically acceptable salts thereof.

4. A compound of claim 3 wherein R, $R_1$ and $R_2$ are each hydrogen, X is oxygen, n is 1 and m is 0.

5. A compound of claim 3 wherein R, $R_1$ and $R_2$ are each hydrogen, X is sulfur, n is 1 and m is 0.

6. A compound of claim 3 wherein R is hydrogen, $R_1$ is phenyl, $R_2$ is hydrogen, X is oxygen, n is 1 and m is 0.

7. A compound of claim 3 wherein R is hydrogen, $R_1$ is methyl, $R_2$ is hydrogen, X is oxygen, n is 1 and m is 0.

8. A compound of claim 3 wherein R is hydrogen, $R_1$ and $R_2$ are each methyl, X is oxygen, n is 1 and m is 0.

9. A compound of claim 3 wherein R is hydrogen, $R_1$ and $R_2$ are each phenyl, X is oxygen, n is 1 and m is 0.

10. A pharmaceutical composition useful for the treatment of inflammatory conditions which comprises a compound of the formula

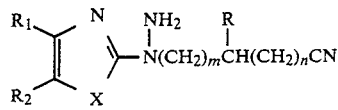

wherein R is hydrogen, $R_1$ and $R_2$ independent of one another denote hydrogen, loweralkyl or phenyl, X is oxygen or sulfur, n is 1 and m is 0, or pharmaceutically acceptable salts thereof, together with a pharmaceutically acceptable carrier.

11. The composition of claim 10 wherein R, $R_1$ and $R_2$ are each hydrogen, X is oxygen, n is 1 and m is 0.

12. The composition of claim 10 wherein R, $R_1$ and $R_2$ are each hydrogen, X is sulfur, n is 1 and m is 0.

13. The composition of claim 10 wherein R is hydrogen, $R_1$ is phenyl, $R_2$ is hydrogen, X is oxygen, n is 1 and n is 0.

14. The composition of claim 10 wherein R is hydrogen, $R_1$ is methyl, $R_2$ is hydrogen, X is oxygen, n is 1 and m is 0.

15. The composition of claim 10 wherein R is hydrogen, $R_1$ and $R_2$ are each methyl, X is oxygen, n is 1 and m is 0.

16. The composition of claim 10 wherein R is hydrogen, $R_1$ and $R_2$ are each phenyl, X is oxygen, n is 1 and m is 0.

17. A method of treating or relieving the symptoms associated with inflammation comprising administering to a patient in need of such treatment a therapeutically effective amount of an anti-inflammatory agent of the formula

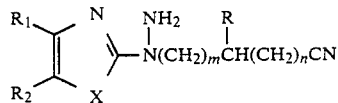

wherein R is hydrogen, $R_1$ and $R_2$ independent of one another denote hydrogen, loweralkyl or phenyl, X is oxygen or sulfur, n is 1 and m is 0, or pharmaceutically acceptable salts thereof.

18. The method of claim 17 wherein R, $R_1$ and $R_2$ are each hydrogen, X is oxygen, n is 1 and m is 0.

19. The method of claim 17 wherein R, $R_1$ and $R_2$ are each hydrogen, X is sulfur, n is 1 and m is 0.

20. The method of claim 17 wherein R is hydrogen, $R_1$ is phenyl, $R_2$ is hydrogen, X is oxygen, n is 1 and m is 0.

21. The method of claim 17 wherein R is hydrogen, $R_1$ is methyl, $R_2$ is hydrogen, X is oxygen, n is 1 and m is 0.

22. The method of claim 17 wherein R is hydrogen, $R_1$ and $R_2$ are each methyl, X is oxygen, n is 1 and m is 0.

23. The method of claim 17 wherein R is hydrogen, $R_1$ and $R_2$ are each phenyl, X is oxygen, n is 1 and m is 0.

* * * * *